US00PP07980P

United States Patent [19]

Twomey

[11] Patent Number: Plant 7,980

[45] Date of Patent: Sep. 22, 1992

[54] HYBRID TEA ROSE PLANT NAMED TWOADORE

[75] Inventor: Jerry Twomey, Leucadia, Calif.

[73] Assignee: DeVor Nurseries, Inc., Watsonville, Calif.

[21] Appl. No.: 640,862

[22] Filed: Jan. 11, 1991

[51] Int. Cl.[5] ..... A01H 5/00

[52] U.S. Cl. ..... Plt./18

[58] Field of Search ..... Plt./18, 11, 19

[56] References Cited

U.S. PATENT DOCUMENTS

P.P. 5,575 10/1985 Kordes et al. ..... Plt. 18

*Primary Examiner*—Howard J. Locker

*Attorney, Agent, or Firm*—Christie, Parker & Hale

[57] ABSTRACT

A new hybrid tea rose plant producing light pink flowers.

1 Drawing Sheet

SUMMARY OF THE INVENTION

The present invention relates to a new and distinct variety of rose plant of the hybrid tea rose class which was originated by my crossing as seed parent the variety known as 'Evening Star' (U.S. Plant Pat. No. 3,432) and as pollen parent an unnamed and unpatented seedling of my creation. The varietal denomination of this new rose is 'Twoadore'.

Among the novel characteristics possessed by this new variety which distinguishes it from its parents and all other varieties of which I am aware are its light pink flowers which are attractive in fully open and partially open stages borne on a plant particularly suitable for use in gardens. Flowers open well and remain attractive as blooms age. The new variety is also characterized by its health, vigor and flower production.

Asexual reproduction by budding and rooting of cuttings of the new variety as performed in Glenn County, Calif. and Kern County, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

'Twoadore' is an unusually fine hybrid tea rose of light pink flower coloration. It is especially well suited for growing outdoor in gardens. The variety blooms freely under natural growing conditions. The foliage is dark green, and semi leathery; providing a good background for the light pink flowers profusely produced.

The following is a detailed description of my new variety, with color terminology in accordance with the Royal Horticultural Society Colour Chart (R.H.S.C.C.). The terminology used in color description herein refers to plate numbers in the aforementioned color chart.

Parentage: Seedling.

*Seed parent.*—'Evening Star'.

*Pollen parent.*—Unnamed seedling.

Class: Hybrid tea.

The following information is from observations made of specimens grown outdoors in Watsonville, Calif.

FLOWER

Blooming habit: Continuous, profuse.

A. Bud:

(1) *Size.*—Medium; about 1.5 to 2 cm in diameter and 2.5 to 3 cm in length.

(2) *Form.*—Globular, pointed at tip, slow opening.

(3) *Color.*—As sepals divide, bud color is near 51B.

(4) *Sepals.*—5 in number; slightly longer than bud; simple to foliaceous; sepals curl back. Color: Inside — near 148C. Outside — near 146B.

(5) *Peduncle.*—Length: 9 cm to 11 cm; small spines. Aspect: Straight, slender. Strength: Erect, rigid. Color: Near 146B.

(6) *Calyx.*—Shape: Funnel shaped; does not split; smooth. Size: Medium; 0.9 to 1 cm×0.7 cm.

B. Bloom:

(2) *Size.*—Average size when fully expanded — about 10 to 11.5 cm; depth about 3.5 cm.

(2) *Borne.*—Singly, one to a stem, disbudded, and in clusters.

(3) *Form.*—Cupped, open bloom displays whorled petal configuration.

(4) *Petalage.*—Number of petals under normal conditions — about 30 to 32; 1 to 3 petaloids.

(5) *Color.*—After sepals fall and petals begin to unfurl, predominant flower color viewing petals' under surface is near 62D to 56D. Petal top surface as seen in fully open bloom is near 36D with near 39B to C at some petal margins. In blooms ¼ to ½ open color appears near 39C to near 37C where petals bunch. Outer petals show washing of near 55C to 55D in upper petal segments and margins on both top and under petal surfaces. Color is general and substantially constant though with darker hues sometimes at petal edges. Petal undersurface displays similar coloration. Color at point of petal attachment is near 8D.

C. Petals:

(1) *Texture.*—Medium to thick.

(2) *Appearance.*—Inside slightly velvety and outside satiny.

(3) *Form.*—Broad, fan shaped with some indentation or undulation at margin (slightly lobed), outer petals quill to points.
(4) *Arrangement.*—Regularly arranged, imbricated.
(5) *Fragrance.*—Moderate.
(6) *Lasting quality.*—Long lasting on plant and as cut flower.

REPRODUCTIVE ORGANS

A. Stamens:
*Number.*—Approximately 260.
*Arrangement.*—Introrse.
*Anthers.*—Size — 0.2 cm. Color — near 13B.
*Filaments.*—(Threads): Length — 1 to 1.2 cm. Color — near 7A.
*Pollen.*—Color — near 21C.

B. Pistils:
*Number.*—Approximately 109.
*Styles.*—Length — 1 cm. Color — near 145C with near 53C at top.
*Stigmas.*—Color — near 21D.

C. Characteristics of ovaries: Small, oblong, slightly flattened with silvery hairs covering.

D. Hips:
*Fertile.*—Yes.
*Shape.*—Globular but depressed at top.
*Color at maturity.*—Near 170B; 2.8 cm wide×2.1 cm long.

PLANT

A. Form: Upright.

B. Growth: Vigorous, upright; free branching; height attained about 145 cm at three years.

C. Foliage: Compound 3, 5 and 7 leaflets.
(1) *Size.*—About 17 cm×12.5 cm.
(2) *Quantity.*—Abundant.

(3) *Color.*—Upper side — dark green. Under side — medium green.
(4) *Shape.*—Oval, pointed.
(5) *Texture.*—Semi-leathery; upper side is glossy, under side is matte.
(6) *Edge.*—Serrate, (denticulate).
(7) *Serration.*—Ordinary.
(8) *Leaf stem.*—Color — medium green.
(9) *Stipules.*—Hairy, adnate.
(10) *Petiolule.*—About 0.2 cm.
(11) *Rachis.*—About 13 cm on 3 leaf; 17 cm on 5 leaf; 19 cm on 7 leaf.
(12) *Petioles.*—Length — 2 cm on 3 leaf; 2.5 cm on 5 and 7 leaf (avg.).
(13) *Ribs and Veins.*—Ribs depressed; ribs and veins slightly rounded underneath. Rachis: Small spines underneath.
(14) *Resistance to disease.*—Resistant to mildew, moderately resistant to rust and black spot.

D. Wood
(1) *New wood.*—Color — medium green. Bark — smooth.
(2) *Old wood.*—Color — near 146B. Bark — smooth.

E. Thorns:
(1) *Thorns.*—Quantity (main stalk) — average. On laterals from stalk — average. Form — thin, curved, angled downward. Length — 1 to 1.5 cm. Color — near 178C at tip. Position — irregular.
(2) *Prickles.*—Few to none present.

F. Winter hardiness: Needs protection in severe climates.

I claim:

1. A new and distinct variety of rose plant of the hybrid tea rose class, substantially as shown and described.

* * * * *

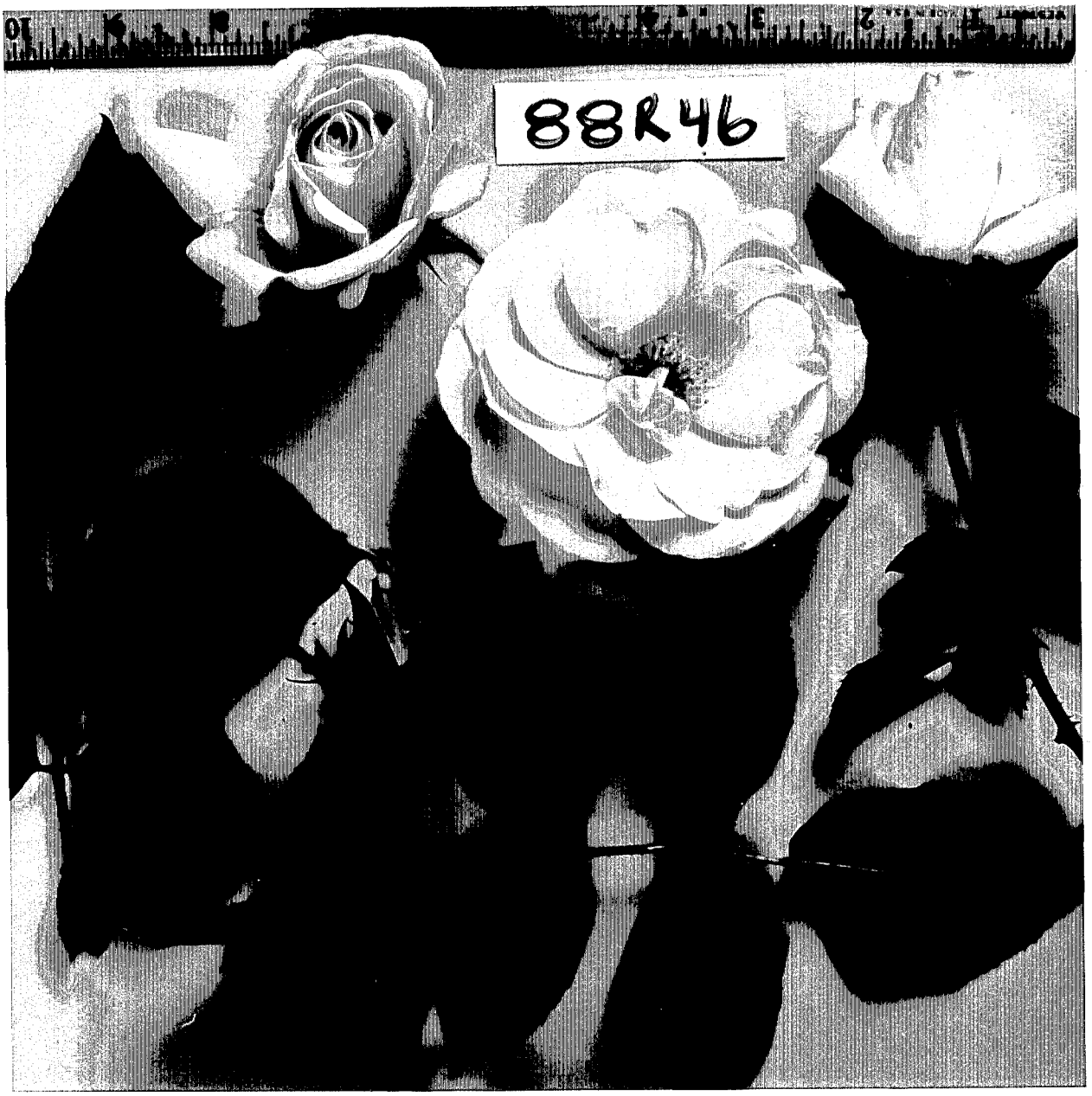
88R46

UNITED STATES PATENT AND TRADEMARK OFFICE

CERTIFICATE OF CORRECTION

PATENT NO. : Plant 7,980

DATED : September 22, 1992

INVENTOR(S) : Jerry Twomey

It is certified that error appears in the above-identified patent and that said Letters Patent is hereby corrected as shown below:

Column 2, line 23, before "Size" change "(2)" to -- (1) --.

Signed and Sealed this

Nineteenth Day of October, 1993

*Attest:*

*Attesting Officer*

BRUCE LEHMAN

*Commissioner of Patents and Trademarks*